United States Patent [19]
Qi et al.

[11] Patent Number: 5,395,961
[45] Date of Patent: Mar. 7, 1995

[54] REDUCING DECOMPOSITION OF ACETATES

[75] Inventors: J. Steven Qi, Amherst; Garra C. Lester, Eden, both of N.Y.

[73] Assignee: Occidental Chemical Corporation, Niagara Falls, N.Y.

[21] Appl. No.: 96,395

[22] Filed: Jul. 26, 1993

[51] Int. Cl.$^6$ ............................................. C07C 67/02
[52] U.S. Cl. .................................. 560/265; 528/935; 525/221; 525/223
[58] Field of Search ...................... 560/265; 528/935; 525/221, 223

[56] References Cited

U.S. PATENT DOCUMENTS

| | | | |
|---|---|---|---|
| 3,857,724 | 12/1974 | Bakos | 427/438 |
| 4,297,258 | 10/1981 | Long, Jr. | 524/200 |
| 4,786,431 | 11/1988 | Broze et al. | 252/99 |
| 5,043,205 | 8/1991 | Perazzo et al. | 428/215 |

FOREIGN PATENT DOCUMENTS

0521488A2  1/1993  European Pat. Off. .

*Primary Examiner*—Arthur C. Prescott
*Attorney, Agent, or Firm*—Wayne A. Jones; Richard D. Fuerle

[57] ABSTRACT

Disclosed is a method of reducing the decomposition of liquid acetates and increasing their storage life. A soluble amine having a pH in water between 9 and 12 is added to the acetate. Also disclosed is a composition of about 1 to about 50 ppm of the amine in the acetate.

20 Claims, No Drawings

REDUCING DECOMPOSITION OF ACETATES

BACKGROUND OF THE INVENTION

This invention relates to a method of reducing the decomposition of liquid acetates by adding soluble amines thereto. In particular, it relates to a composition of an acetate and a very small amount of a soluble amine, which increases the storage life of the acetate.

Commercial quantities of various acetates are made by reacting the corresponding alcohol with acetic acid. For example, ethylene glycol monobutylether acetate (EBA) is made commercially according to the following reversible reaction:

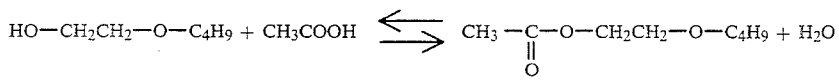

Fractional distillation is used to separate the product from the reactants and from the water that is formed. Once the product has been separated, it must be carefully handled and kept from all contact with water. Even the moisture in the air is enough to reverse the reaction and form acetic acid.

The acetates are used in various lacquers and the presence of acetic acid in the lacquer can cause corrosion and adherence problems, change surface properties, and adversely affect the stability of the lacquer product. Acetate users have set specifications for industrial acetates that require less than 200 ppm of acetic acid and less than 2000 ppm water. Although acetates meet the specifications when they are manufactured, by the time they are transported to the customer and are unloaded they often exceed the required specifications. Acetates that do not meet the specifications must be sold at steep discounts or returned to the manufacturer to undergo a costly purification process.

Many efforts have been made to solve this problem. It was suspected that the problem may be related to decomposition of the sulfonic acid type of catalyst used in manufacturing the acetate, such as p-toluene sulfonic acid. However, evidence supporting this mechanism has rarely been found in literature. Nonetheless, different distillation schemes have been tried to determine whether acetates purified are more stable. (See, for example, EP Application 521,488.) While the distillation schemes claimed in EP Application 521,488 appear to increase stability, the improved stability may be due to less moisture and it is impractical for acetate manufacturers to adapt the existing equipment to the new and more complicated scheme. It has also been proposed to add various hygroscopic or moisture-absorbing materials to the acetates, but as yet no such material has been found which is both effective and acceptable to the users of the acetates.

SUMMARY OF THE INVENTION

We have discovered that liquid acetates can be stabilized and prevented from rapidly decomposing to form acetic acid if a very small amount of an amine is added to the acetate. Since the amount of amine added is so small (less than 50 ppm) we are unable to explain how it prevents decomposition because such a small amount would normally be quickly overwhelmed by whatever is causing the decomposition. That is, even when the acetates are exposed to as much as 1000 ppm of water, the presence of less than 50 ppm of the amine still prevents the formation of acetic acid. Nor does the amine work by reacting with acetic acid that is being formed, because the amine is effective in reducing the formation of acetic acid even when the acetic acid is being formed at a rate that would quickly overwhelm the amount of amine that is present. At the present time, we are unable to explain why amines are effective in stabilizing acetates.

DESCRIPTION OF THE INVENTION

This invention is applicable to any liquid acetate, but is particularly applicable to liquid acetates having the formula

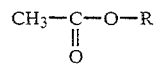

where R is aliphatic from $C_2$ to $C_{10}$, which includes glycol ethers. Examples of such acetates include ethylene glycol monobutylether acetate (EBA, also known as butyl cellosolve acetate), diethylene glycol monoethyl ether acetate (also known as carbitol acetate), diethylene glycol monobutyl ether acetate (DBA, also known as butyl carbitol acetate), propylene glycol monomethyl ether acetate, methyl acetate, ethyl acetate, isopropyl acetate, n-propyl acetate, sec-butyl acetate, isobutyl acetate, n-butyl acetate, isobutyl isobutyrate, ethylene glycol monomethylether acetate, and ethylene glycol monoethylether acetate (EEA). The preferred acetates are EEA, DBA, EBA, and butyl acetate because they are or may be commercial products and are particularly susceptible to the problem of decomposition. The invention is also particularly applicable to acetates made with p-toluene sulfonic acid because products made with that catalyst tend to be unstable and more susceptible to decomposition.

Amines useful in this invention include organic primary, secondary, and tertiary amines, provided the amine is soluble in the particular liquid acetate being protected. The amine should also have a pH in water between 9 and 12. Amines that are too basic (i.e., have a pH greater than 12 in water) may discolor the acetate and amines that are insufficiently basic (i.e., have a pH of less than 9 in water) are not very effective. Preferred amines have the formula $R_1$—NH—$R_2$ where $R_1$ is aromatic or aliphatic from $C_1$ to $C_{15}$ and $R_2$ is $R_1$ or hydrogen; $R_1$ is preferably $C_1$ to $C_4$. Particularly preferred are hydroxyamines such as monoethanolamine (MEA), which have the formula $NH_2$—$R_1$—OH, as they are more soluble in acetates and are very effective. Examples of suitable amines include aniline, hydroxyaniline, monoethanolamine, propylamine, butylamine, triethylamine and triethanolamine. Any concentration of amine between 1 and 50 ppm can be used. We have found that at a concentration of less than 1 ppm the amine has little effect in preventing the decomposition of the acetate and that at more than 50 ppm no additional protection is provided and the amine may make the acetate turbid. It is preferable to use about 30 to about 40 ppm of the amine in stabilizing acetates.

It is preferable not to mix the composition of the acetate and the amine with any other substances as other substances may interfere with the effectiveness of the amine in preventing decomposition or may be unacceptable to customers. The composition of the acetate and amine can be used in multi-color lacquers and lacquer emulsions, as coalescing aids for latex paints, and as a retarder solvent in the formulation of high-low lacquer thinners, printing inks, and epoxy coatings.

The following examples further illustrate this invention. In these examples the acetic acid value was determined in a procedure similar to the ASTM D1639 titration method. That is, a sample was first mixed with 100 mL of a mixture of isopropanol and toluene in a 1:1 ratio by volume which had been neutralized with a methanol solution of 0.1 N KOH using a phenolphthalein indicator. The mixture containing the sample was then titrated with the 0.1 N KOH solution to the end point, which was a pink color persisting for 30 seconds. All of these experiments were performed at room temperature (20° C.).

EXAMPLE 1

This example illustrates the hygroscopic properties EBA, DBA and EEA. Several 100 mL glass beakers each filled with about 20 mL EBA, DBA or EEA, were exposed to air at 20° C. having a relative humidity of 50 percent. The beakers had an inside diameter of 5 cm and therefore the exposed area of acetate was about 20 cm$^2$. After a selected exposure time, the average moisture content of the acetate in each beaker was measured to obtain the moisture absorption rate for the acetate. The table below lists the data and the results of this experiment.

| Exposure time (min) | 0 | 15 | 30 | 80 | 120 |
| --- | --- | --- | --- | --- | --- |
| ppm water in EBA | 150 | 2700 | 5200 | 7100 | 9100 |
| ppm water in DBA | 300 | 1400 | 2200 | 3800 | 5600 |
| ppm water in EEA | 100 | 1600 | 2100 | 3700 | 4100 |

The table shows that after only 15 minutes of exposure to air the moisture content of the acetate increased many times.

EXAMPLE 2

This example illustrates the hydrolysis rate of a commercially produced EBA. A commercial EBA (purity=99.1%, 0.4% ethylene glycol monobutyl ether and 0.3% ethylene glycol diacetate) having an initial acidity of 89 ppm acetic acid and 160 ppm water was stored in a tightly sealed container at room temperature. After 53 days the acetic acid level increased to 408 ppm. The acetic acid level continued to increase to 502 ppm after 69 days. (Hydrolysis rate=6 ppm/day.) After this, the EBA was spiked with 1000 ppm of water and the acetic acid level increased by nearly 1000 ppm over just a short 8-day period, producing a hydrolysis rate of 125 ppm/day. After an additional sixteen days of storage another 1300 ppm of acetic acid was produced.

EXAMPLE 3

This example is similar to Example 2 except that 400 ppm monoethanolamine was also added to the EBA along with the 1000 ppm water. The acidity was analyzed right after the addition and indicated essentially no change. After addition of the monoethanolamine the EBA hydrolysis rate over the initial sixteen days of storage was below 3 ppm/day. The rate was then reduced to about 0.3 ppm/day during an additional 39 days (average hydrolysis rate over the total 55-day period was about 1 ppm/day, a significant reduction from the hydrolysis rate of 125 ppm/day). Note that the stability created by the addition of the monoethanolamine was not due to its reaction with acetic acid because, as Example 2 showed, acetic acid generated at 125 ppm/day would far exceed what the amine could neutralize.

EXAMPLE 4

This example is similar to Example 3 but only 40 ppm monoethanolamine was added. The increase in acetic acid level was less than 5 ppm over the first sixteen day period. Re-analysis of this EBA after another five months showed only an additional 35 ppm increase in the acetic acid level. The average hydrolysis rate was less than 0.3 ppm/day.

EXAMPLE 5

This example is similar to Example 3 except that only 10 ppm monoethanolamine was added. The increase in the acetic acid level was about 400 ppm over an eight day period. The average hydrolysis rate was roughly 50 ppm/day. This example indicates that the amount of amine is important. If not enough amine is used hydrolysis will still take place, although at a pace far slower than if no amine were added.

EXAMPLE 6

An EBA product having a purity of 99.3 wt % (0.5% EB, 0.1% ethylene glycol diacetate), a moisture level of 175 ppm and an acetic acid level of 41 ppm was sealed in a bottle and stored at room temperature for about 9 months. The acetic acid level increased to 274 ppm. To samples of that product was added 1000 ppm of water with or without 40 ppm of various amines and the acetic acid levels were measured after 13 days. The following table gives the results:

| Amine | Acetic Acid Level (ppm) | Change In Acetic Acid Level (ppm) | Hydrolysis Rate (ppm/day) |
| --- | --- | --- | --- |
| None | 629 | +355 | 27 |
| Monoethanolamine | 273 | −1 | 0 |
| Propylamine | 281 | +7 | 0.5 |
| Triethylamine | 286 | +12 | 0.9 |
| Aniline | 288 | +14 | 1.1 |

The table shows that all of the amines tested were effective and that monoethanolamine was the most effective.

EXAMPLE 7

DBA was synthesized using diethylene glycol monobutyl ether (DB) and acetic acid. 324 g of DB, 144 g of acetic acid, 75 g octane, and 0.26 g reagent grade p-toluene sulfonic acid monohydride were charged to a reactor. After the by-product water was removed by octane azeotrope distillation and the DB was completely reacted the DBA product was isolated and purified to 99.0% by careful fractional distillations using a 20 plate Oldershaw column. The DBA produced contained about 0.5% DB but only 28 ppm acetic acid.

The DBA was then stored in a tightly sealed container. After 25 days, the acetic acid level increased to 42 ppm; and after 55 days, it increased to 61 ppm (about 0.6 ppm/day). After this, the DBA was spiked with 1,000 ppm water and the acid level increased to 91 ppm within 20 days, i.e., the hydrolysis rate increased to 1.5 ppm/day after the water addition. However, when 40 ppm monoethanolamine was added at the same time, the acidity increased to only 73 ppm over the same period, reducing the hydrolysis rate to 0.6 ppm/day.

We claim:

1. A method of reducing the decomposition of a liquid acetate comprising adding thereto about 1 to about 50 ppm of an amine soluble therein which has a pH in water between 9 and 12.

2. A method according to claim 1 wherein said liquid acetate has the formula

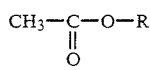

where R is aliphatic from $C_2$ to $C_{10}$.

3. A method according to claim 1 wherein said liquid acetate is ethylene glycol monobutyl ether acetate.

4. A method according to claim 1 wherein said liquid acetate is diethylene glycol monobutyl ether acetate.

5. A method according to claim 1 wherein said liquid acetate is ethylene glycol monoethyl ether acetate.

6. A method according to claim 1 wherein said liquid acetate is butyl acetate.

7. A method according to claim 1 wherein said liquid acetate is made using p-toluene sulfonic acid as a catalyst.

8. A method according to claim 1 wherein said amine is a hydroxyamine.

9. A method according to claim 1 wherein said amine is monoethanolamine.

10. A method according to claim 1 wherein said amine has the formula $NH_2-R_1-OH$ where $R_1$ is aromatic or aliphatic from $C_1$ to $C_{15}$.

11. A method of increasing the storage life of a liquid acetate having the formula

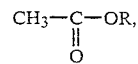

where R is aliphatic from $C_2$ to $C_{10}$, comprising adding to said liquid acetate about 30 to about 40 ppm of an amine soluble therein having a pH in water between 9 and 12 and having the formula $NH_2-R_1-OH$ where $R_1$ is alkyl from $C_1$ to $C_4$.

12. A method according to claim 11 wherein said liquid acetate is ethylene glycol monobutyl ether acetate.

13. A method according to claim 11 wherein said liquid acetate is diethylene glycol monobutyl ether acetate.

14. A method according to claim 11 wherein said liquid acetate is ethylene glycol monoethyl ether acetate.

15. A method according to claim 11 wherein said liquid acetate is butyl acetate.

16. A method according to claim 11 wherein said liquid acetate is made using p-toluene sulfonic acid as a catalyst.

17. A method according to claim 11 wherein said amine is a hydroxyamine.

18. A method according to claim 11 wherein said amine is monoethanolamine.

19. A composition comprising a liquid acetate and about 1 to about 50 ppm of an amine soluble therein which has a pH in water between 9 and 12.

20. A composition according to claim 17 wherein said amine is a hydroxyamine.

* * * * *